United States Patent [19]

Erpenbach et al.

[11] Patent Number: 5,002,914

[45] Date of Patent: Mar. 26, 1991

[54] PROCESS FOR PURIFYING AND RECOVERING THE CONTAMINATED CATALYST SOLUTION ARISING IN THE CARBONYLATION OF METHANOL AND/OR METHYL ACETATE AND/OR DIMETHYL ETHER

[75] Inventors: Heinz Erpenbach, Cologne; Winfried Lork, Erftstadt; Norbert Weferling; Peter Prinz, both of Hürth, all of Fed. Rep. of Germany

[73] Assignee: Hoechst Aktiengesellschaft, Frankfurt am Main, Fed. Rep. of Germany

[21] Appl. No.: 491,352

[22] Filed: Mar. 9, 1990

[30] Foreign Application Priority Data

Mar. 22, 1989 [DE] Fed. Rep. of Germany ....... 3909445

[51] Int. Cl.$^5$ .................. B01J 38/68; B01J 31/40; C07C 53/08; C07B 41/08
[52] U.S. Cl. ......................... 502/24; 502/31; 502/33; 560/232; 562/517; 562/890; 562/891
[58] Field of Search ............... 502/24, 22, 33, 31; 423/22; 562/898, 891

[56] References Cited

U.S. PATENT DOCUMENTS

| | | | |
|---|---|---|---|
| 4,143,066 | 3/1979 | Kalcevic | 562/513 |
| 4,297,239 | 10/1981 | Bryant et al. | 502/24 |
| 4,298,499 | 11/1981 | Imai | 502/24 |
| 4,371,509 | 2/1985 | Grosse | 423/300 |
| 4,629,711 | 12/1986 | Erpenbach et al. | 502/24 |
| 4,650,615 | 3/1987 | Rizkalla | 562/898 |
| 4,746,640 | 5/1988 | Erpenbach et al. | 502/24 |
| 4,795,594 | 1/1989 | Dankowski | 562/6 |

*Primary Examiner*—Paul E. Konopka

[57] ABSTRACT

A process for purifying and recovering the contaminated catalyst solution arising from the carbonylation of methanol, methyl acetate and/or dimethyl ether. The solution contains carbonyl complexes of rhodium, quaternary organophosphorus compounds as organic promoters, undistillable organic impurities, and acetic acid, acetic anhydride and ethylidene diacetate. The carbonyl complex of rhodium together with acetic acid, acetic anhydride and ethylidene diacetate are extracted from the contaminated catalyst solution by using a tri-$C_3$- to $C_8$-alkylphosphine. The trialkylphosphine phase is separated from the promoter phase and is separated into the volatile constituents acetic acid, acetic anhydride and ethylidene diacetate as well as trialkylphosphine. The rhodium carbonyl complex remaining as the residue and the recovered trialkylphosphine is used for further extraction. The contaminated promoter phase is freed of the organic impurities by extraction with dialkyl ethers, carboxylic acid esters or hydrocarbons and, after the extractant phase has been separated off, is recombined with the recovered acetic acid/acetic anhydride and ethylidene diacetate mixture and with the rhodium carbonyl complex and recycled to the carbonylation reactor. The impurities remaining as the residue from a distillation of the extractant phase which has been separated off are removed from the system.

4 Claims, No Drawings

PROCESS FOR PURIFYING AND RECOVERING THE CONTAMINATED CATALYST SOLUTION ARISING IN THE CARBONYLATION OF METHANOL AND/OR METHYL ACETATE AND/OR DIMETHYL ETHER

The invention relates to a process for purifying and recovering the contaminated catalyst solution arising in the carbonylation of methanol and/or methyl acetate and/or dimethyl ether and containing carbonyl complexes of rhodium, quaternary organophosphorus compounds as organic promoters, undistillable organic impurities as well as acetic acid, acetic anhydride and ethylidene diacetate.

For carrying out hydroformylation and carbonylation processes, rhodium is used as the rare metal catalyst in the form of diverse complex compounds. Since rhodium is a very expensive rare metal, because of its low availability, there are several reports in the literature on its recovery or the purification of rhodium complexes from catalyst systems and distillation bottoms, contaminated with residues, from the abovementioned reactions.

EP-A-0,240,703 (=U.S. Pat. No. 4,746,640) claims a process which permits purification of the contaminated rhodium-containing catalyst solution arising in the carbonylation of methyl acetate and/or dimethyl ether, in such a way that the undistillable organic residues, formed during the reaction, are removed from the solution by a liquid/liquid extraction with dialkyl ethers and alkanols each having 1-4 carbon atoms. The ether phase containing the organic residues is subjected to an aftertreatment with iodine and/or methyl iodide, separated off from the precipitated residual catalyst complex and then further separated by distillation into dialkyl ether to be reused and alkanol to be reused as well as acetic acid, acetic anhydride, ethylidene diacetate and undistillable residue. The acetic acid, acetic anhydride and ethylidene diacetate are combined with the purified catalyst phase and the catalyst complex isolated from the ether phase, freed of the remaining ether and alcohol and fed as fresh catalyst solution to the reaction. Only <0.1% of the rhodium introduced into the extraction remains in the ether phase distillation residue which is removed from the system.

The high price of rhodium allows only loss-free use as a catalyst for large-scale industrial processes. This also applies to the purification and recovery of a spent contaminated rhodium catalyst and therefore makes quantitative recycle imperative. This requires a separation of the organic residue formed in the process from the catalyst solution without any Rh loss and direct reintroduction of the purified catalyst system into the reaction.

The process of EP-A-0,240,703 (=U.S. Pat. No. 4,746,640) fully meets the stated requirements and, at 99.9%, shows a very good rhodium recovery rate. However, it demands an additional aftertreatment of the ether phase with iodine and subsequent separation of the treatment products. The present invention now describes a process which allows a purification of the catalyst solution, used in the carbonylation of methanol and/or methyl acetate and/or dimethyl ether and contaminated in the course of the process, by extraction with a trialkylphosphine, wherein the separation of the undistillable organic impurities from the catalyst solution takes place without rhodium loss and without destruction of the rhodium carbonyl complex and the promoter. The Rh complex and the promoter can be recycled to the carbonylation process without additional measures. Pollution of the environment by waste materials is avoided by operating with circulation of the trialkylphosphine extractant employed for the reprocessing. Only the organic impurities formed in the process are removed from the system and can be eliminated in accordance with the state of the art. The extraction method of the process of the invention can be carried out in the form of a liquid/liquid extraction. A continuous procedure is feasible in any extraction apparatus according to the state of the art. Extraction in, for example, a counter-current column here allows the quantity of extractant to be minimized.

In detail, the process of the invention now comprises extracting the carbonyl complex of rhodium as well as acetic acid, acetic anhydride and ethylidene diacetate from the contaminated catalyst solution by means of a trialkylphosphine of the formula $R^1R^2R^3P$, in which $R^1$, $R^2$ and $R^3$ are identical or different and are $C_3$- to $C_8$-alkyl, and separating the trialkylphosphine phase from the promoter phase freed of rhodium and containing the organic impurities; separating the trialkylphosphine phase into the volatile constituents acetic acid, acetic anhydride and ethylidene diacetate as well as trialkylphosphine and the carbonyl complex of rhodium remaining as the residue; using the recovered trialkylphosphine for further extraction; freeing the contaminated promoter phase, freed of the carbonyl complex of rhodium, of the organic impurities by extraction with dialkyl ethers, carboxylic acid esters or hydrocarbons and, after the extractant phase has been separated off, recombining it with the recovered mixture of acetic acid, acetic anhydride and ethylidene diacetate and with the carbonyl complex of rhodium and feeding it to the carbonylation reactor; and removing the organic impurities, remaining as the residue from the distillation of the extractant phase which has been separated off, from the system.

Preferably and selectively, the process of the invention can also comprise (a) carrying out the extraction of the contaminated catalyst solution with trialkylphosphine at temperatures of 20°–100° C.;

(b) using 0.5–10 parts by weight of a trialkylphosphine per part by weight of contaminated catalyst solution;

(c) adding 0.03–0.4 part by weight of methanol per part by weight of contaminated catalyst solution;

(d) first distilling off the volatile constituents acetic acid, acetic anhydride and ethylidene diacetate from the contaminated catalyst solution, then extracting the distillation residue with trialkylphosphine with an addition of methanol and separating the two-phase mixture formed into a purified trialkylphosphine phase containing the carbonyl complex of rhodium and a promoter phase containing organic impurities, and further proceeding as described above; and (e) using tri-n-butylphosphine, tri-n-octylphosphine or 2-butyl-di-n-octylphosphine as the trialkylphosphine.

The reaction mixture flowing out of a carbonylation reactor is separated by distillation into, on the one hand, the desired end products, especially acetic anhydride and acetic acid, and unconverted, circulated starting materials and, on the other hand, the catalyst solution arising as the bottom product and circulated. A part stream of this catalyst solution which is contaminated in the course of time by undistillable organic products and which, depending on the process conditions, can contain up to 75 M-% (=% by mass) of acetic anhydride, acetic acid and/or ethylidene diacetate, is taken out of the circulation of the catalyst solution and passed to purification. The catalyst solution contains the rare metal rhodium as a carbonyl complex such as, for example

The catalyst solution can also contain preferably tri-n-butyl-methyl-phosphonium iodide or tetra-n-butyl-phosphonium iodide as organic promoters.

The contaminated catalyst solution, which has been removed from the system, is extracted with a trialkyl-phosphine preferably at 20° to 100° C. The rhodium carbonyl complex and the fractions of acetic acid (AcOH), acetic anhydride (Ac$_2$O) and ethylidene diacetate (EDA) in the catalyst solution are thus extracted, while the undistillable organic impurities with the promoter remain as the promoter phase. From the trialkylphosphine (TAP) phase, the AcOH/Ac$_2$O/EDA mixture and the TAP are recovered by distillation, while the rhodium carbonyl complex is obtained as the residue. The TAP is re-used again for extraction. The organic impurities are removed from the promoter phase by means of extraction with, for example, methyl acetate or di-i-propyl ether. The promoter phase freed of the residue is then combined with the redistilled AcOH-/Ac$_2$O/EDA mixture and the purified rhodium carbonyl complex, which has remained as the distillation residue, and recycled as purified catalyst solution to the carbonylation. After the extractant methyl acetate or di-i-propyl ether has been separated off, the organic impurities are destroyed, for example in an incinerator unit. The recovered extractants are re-used. The process of the invention can be carried out either in a continuous or discontinuous operating procedure.

EXAMPLE 1

To remove the organic impurities, 500 g of catalyst solution of the composition 6.1 M-% of rhodium carbonyl complex [CH$_3$P(C$_4$H$_9$)$_3$] [Rh(CO)$_2$I$_2$] ($\hat{=}$5.0 g of Rh=1.0 M-%), 65.5 M-% of methyl-tri-n-butylphosphonium iodide (TBPMeI), 3.0 M-% of organic impurities and 25.4 M-% of a mixture of acetic acid, acetic anhydride and ethylidene diacetate are taken from the catalyst circulation of the methyl acetate carbonylation and extracted at 35° C. with 1,200 g of tri-n-butylphosphine (TBP). The TBP phase is separated off from the promoter phase and separated by distillation into an acetic acid/aceticanhydride/ethylidene diacetate mixture, tri-n-butylphosphine and rhodium carbonyl complex. The redistilled tri-n-butylphosphine is used for further extraction. From the TBPMeI phase (promoter phase), 13.5 g of organic impurities are removed as a residue (Rh content <0.01%) by extraction with 750 ml of methyl acetate, separation and subsequent distillation of the methyl acetate phase. The methyl acetate thus recovered is used for further extraction. The distillate, obtained from the TBP phase, of 127 g of acetic acid/acetic anhydride/ethylidene diacetate mixture is combined with the rhodium carbonyl complex, freed of the organic impurities, and the purified TBPMeI phase and recycled as 487 g of purified solution having a rhodium content of 5 g to the catalyst circulation. The recycle rate of rhodium into the carbonylation process is >99.97% after the purification of the contaminated catalyst solution taken off.

EXAMPLE 2

To remove the organic impurities, 500 g of catalyst solution of the composition 6.9 M-% of rhodium carbonyl complex [CH$_3$P(C$_4$H$_9$)$_3$] [Rh(CO)I$_4$] ($\hat{=}$4.0 g of RH=0.8 M-%), 55.3 M-% of methyl-tri-n-butylphosphonium iodide (TBPMeI), 2.4 M-% of organic impurities and 35.4% of a mixture of acetic acid, acetic anhydride and ethylidene diacetate are taken from the catalyst circulation of the methanol/methyl acetate carbonylation and extracted at 25° C. with 1,000 g of tri-n-butylphosphine (TBP) with addition of 60 g of methanol. The TBP phase is separated from the TBPMeI phase (promoter phase) and separated by distillation into an acetic acid/acetic anhydride/ethylidene diacetate mixture, tri-n-butylphosphine and rhodium carbonyl complex. The redistilled TBP is used for further extraction. From the TBPMeI phase, 10.7 g of organic impurities are removed as the residue (Rh content <0.01%) by extraction with 1,000 ml of di-i-propyl ether, separation and subsequent distillation of the di-i-propyl ether phase. The methanol thus recovered and the di-i-propyl ether are recycled into the appropriate extraction stage. The distillate, obtained from the TBP phase, of 177 g of acetic acid/acetic anhydride/ethylidene diacetate mixture is combined with the rhodium carbonyl complex, freed of the organic impurities, and the purified TBPMeI phase and recycled as 489 g of purified solution having a rhodium content of 4 g to the catalyst circulation. The recycle rate of the rhodium into the carbonylation process is >99.97% after the purification of the contaminated catalyst solution taken off.

EXAMPLE 3

To remove the organic impurities, 500 g of catalyst solution of the composition 6.1 M-% of rhodium carbonyl complex [CH$_3$P(C$_4$H$_9$)$_3$] [Rh(CO)$_2$I$_2$] (corresponding to 5 g of rhodium=1.0 M-%), 65.0 M-% of methyl-tri-n-butylphosphonium iodide (TBPMeI), 3.0 M-% of organic impurities and 25.9 M-% of a mixture of acetic acid and acetic anhydride are taken from the catalyst circulation of the methanol/methyl acetate carbonylation and extracted at 60° C. with 1000 g of tri-n-octylphosphine (TOP). The TOP phase is separated from the promoter phase and separated by distillation into an acetic acid/acetic anhydride mixture, tri-n-octylphosphine and rhodium carbonyl complex. The redistilled tri-n-octylphosphine is used for further extraction. From the TBPMeI phase (promoter phase), 13.5 g of organic impurities are removed as the residue (Rh content <0.01%) by extraction with 800 ml of methyl acetate, separation and subsequent distillation of the methyl acetate phase. The methyl acetate thus recovered is used for further extraction. The distillate, obtained from the TOP phase, of 129 g of acetic acid/acetic anhydride mixture is combined with the rhodium carbonyl complex, freed of the organic impurities, and the purified TBPMeI phase and recycled as 487 g of purified solution having a rhodium content of 5 g to the catalyst circulation. The recycle rate of the rhodium into the carbonylation process is >99.97% after the purification of the contaminated catalyst solution taken off.

EXAMPLE 4

To remove the organic impurities, 500 g of catalyst solution of the composition 6.9 M-% of rhodium carbonyl complex $[CH_3P(C_4H_9)_3][Rh(CO)I_4]$ (corresponding to 4 g of rhodium=0.8 M-%), 59.0 M-% of methyl-tri-n-butylphosphonium iodide (TBPMeI), 2.4 M-% of organic impurities and 31.7 M-% of a mixture of acetic acid and acetic anhydride are taken from the catalyst circulation of the methanol/methyl acetate carbonylation and extracted at 50° C. with 1,100 g of 2-butyl-di-n-octylphosphine (BDOP). The BDOP phase is separated from the TPBMeI phase (promoter phase) and separated by distillation into an acetic acid/acetic anhydride mixture, 2-butyl-di-n-octylphosphine and rhodium carbonyl complex. The redistilled BDOP is used for further extraction. From the TBPMeI phase, 10.7 g of organic impurities are removed as a residue (Rh content <0.01%) by extraction with 900 ml of diisopropyl ether, separation and subsequent distillation of the diisopropyl ether phase. The recovered diisopropyl ether is recycled to the extraction stage. The distillate, obtained from the BDOP phase, of 158 g of acetic acid/acetic anhydride mixture is combined with the rhodium carbonyl complex, freed of the organic impurities, and the purified TBPMeI phase and recycled as 489 g of purified solution having a rhodium content of 4 g to the catalyst circulation. The recycle rate of the rhodium into the carbonylation process is >99.97% after the purification of the contaminated catalyst solution taken off.

We claim:

1. A process for purifying and recovering the contaminated catalyst solution arising in the carbonylation of methanol, methyl acetate, dimethyl ether or mixtures thereof and containing carbonyl complexes of rhodium, quaternary organophosphorus compounds as organic promoters, undistillable organic impurities as well as acetic acid, acetic anhydride and ethylidene diacetate, which comprises extracting at a temperature between 20° and 100° C. the carbonyl complex of rhodium as well as acetic acid, acetic anhydride and ethylidene diacetate from the contaminated catalyst solution using 0.5 to 10 parts by weight, per part by weight of the contaminated catalyst solution, of a trialkylphosphine of the formula $R^1R^2R^3P$, in which $R^1$, $R^2$ and $R^3$ are identical or different and represent $C_3$-$C_8$-alkyl; separating the trialkylphosphine phase from the promoter phase freed of rhodium and containing the inorganic impurities; separating the trialkylphosphine phase into the volatile constituents acetic acid, acetic anhydride and ethylidene diacetate as well as trialkylphosphine and the carbonyl complex of rhodium remaining as the residue; using the recovered trialkylphosphine for further extraction; freeing the contaminated promoter phase, freed of the carbonyl complex of rhodium, of the organic impurities by extraction with dialkyl ethers, carboxylic acid esters or hydrocarbons; separating off the extractant phase and recombining the promoter phase with the recovered mixture of acetic acid, acetic anhydride and ethylidene diacetate and with the carbonyl complex of rhodium and feeding it to the carbonylation reactor; and distilling the extractant phase to remove the inorganic impurities as a residue and removing the residue from the system.

2. The process as claimed in claim 1, wherein 0.03 to 0.4 part by weight of methanol is added per part by weight of contaminated catalyst solution.

3. The process as claimed in claim 1, wherein the volatile constituents acetic acid, acetic anhydride and ethylidene diacetate are first distilled off from the contaminated catalyst solution, the distillation residue is then extracted with trialkylphosphine with an addition of methanol and the two-phase mixture formed is separated into a purified trialkylphosphine phase containing the carbonyl complex of rhodium and a promoter phase containing organic impurities, and the further procedure is as claimed in claim 1.

4. The process as claimed in claim 1, wherein the trialkylphosphine is selected from tri-n-butylphosphine, tri-n-octylphosphine or 2-butyl-di-n-octylphosphine.

* * * * *